(12) United States Patent
Ooshima et al.

(10) Patent No.: US 6,561,972 B2
(45) Date of Patent: May 13, 2003

(54) VIDEO SCOPE FOR SIMULTANEOUSLY IMAGING A PORTION FROM MULTIPLE DIRECTIONS

(75) Inventors: Kiyoko Ooshima, Shijonawate (JP); Shinji Uchida, Neyagawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 114 days.

(21) Appl. No.: 09/820,157

(22) Filed: Mar. 28, 2001

(65) Prior Publication Data
US 2001/0026315 A1 Oct. 4, 2001

(30) Foreign Application Priority Data

Mar. 29, 2000 (JP) ........................................ 2000-090340

(51) Int. Cl.⁷ .............................. A61B 1/05; A61B 1/24
(52) U.S. Cl. ...................... 600/173; 600/129; 600/109; 348/66
(58) Field of Search ................................. 600/113, 109, 600/129, 103, 173; 433/29, 30; 348/66, 65, 159, 139

(56) References Cited

U.S. PATENT DOCUMENTS

| | | | | |
|---|---|---|---|---|
| 4,915,626 A | * | 4/1990 | Lemmey ...................... 348/335 |
| 5,027,138 A | * | 6/1991 | Gandrud ....................... 348/66 |
| 5,166,787 A | * | 11/1992 | Irion ............................. 348/75 |
| 5,328,365 A | * | 7/1994 | Jacoby ......................... 433/29 |
| 5,368,015 A | * | 11/1994 | Wilk ............................ 128/903 |
| 5,547,455 A | * | 8/1996 | McKenna et al. .............. 348/65 |
| 5,653,677 A | * | 8/1997 | Okada et al. ................ 600/111 |
| 5,745,165 A | | 4/1998 | Atsuta et al. |
| 5,940,126 A | * | 8/1999 | Kimura ..................... 348/218.1 |
| 5,976,076 A | | 11/1999 | Kolff et al. |
| 6,066,090 A | * | 5/2000 | Yoon ........................... 600/113 |

FOREIGN PATENT DOCUMENTS

| | | |
|---|---|---|
| DE | 4307411 A1 | 9/1994 |
| EP | 0 123 548 | 10/1984 |
| JP | 405115425 | * 5/1993 |
| JP | 8-332170 | 12/1996 |
| JP | 10179516 | 7/1998 |
| JP | 11137512 | 5/1999 |
| WO | WO 94/13190 | 6/1994 |
| WO | WO 98/29050 | 7/1998 |

* cited by examiner

Primary Examiner—John P. Leubecker
(74) Attorney, Agent, or Firm—RatnerPrestia

(57) ABSTRACT

A video scope for simultaneously imaging a portion of the interior of an oral cavity from multiple directions. An entering portion, at its tip end, is bent. The tip end has a U-shaped pickup holding portion having a central portion and two wing portions. An inner wall of the central portion has an incident window capable of guiding image pickup light. There is a CCD unit, an objective lens, and an LED as a light source inside the central portion and the wings. A camera circuit in the grip of the scope operates the CCD unit and a video output cable is connected from the grip portion to a display such as a TV monitor.

4 Claims, 5 Drawing Sheets

VIDEO SCOPE FOR SIMULTANEOUSLY IMAGING A PORTION FROM MULTIPLE DIRECTIONS

BACKGROUND OF THE INVENTION

1. Field of the Invention

The present invention relates to a video scope incorporating a solid state imaging device such as a CCD, and more particularly to a video scope to be used for photographing a diseased part within an oral cavity during dental surgery, in a dental surgical department, or the like.

2. Description of the Related Art

In recent years, during dental surgery, or in a dental surgical department or the like, the art has advanced from medical treatment to prevention. A preventive medical examination first requires an understanding of the state of the interior of a patient's oral cavity. In order to understand the oral cavity, a photograph of the interior of the oral cavity has been taken using a video scope with a solid state imaging device such as a CCD, and the photograph has been preserved as a record.

Also, conventionally, a dental mirror with a small diameter was generally used at the time of examining the state of the interior of the oral cavity during dental surgery. In recent years, a video scope using a solid state imaging device such as CCD has been put to practical use by showing to a patient an image of the interior of an oral cavity on a TV monitor in order to obtain informed consent.

Such a conventional video scope uses a video scope, held in one hand, to pick up a tooth in the oral cavity or by inserting the tip end portion into the oral cavity as disclosed in Japanese Patent Laid-Open No. 8-332170 (U.S. Pat. No. 5,745,165).

However, a conventional video scope photographs one tooth or a plurality of teeth in one direction through a pickup incident window provided at a place on the side, the inclined plane of the tip end or the end surface thereof. The problem is that in order to pick up the inner part (the back side) of the oral cavity, the lip side (the surface side) and the clenched teeth surface side for all teeth, a great number of movements and image pickups are needed, which takes a lot of time.

Also, since the back side, the surface side and the clenched teeth surface side of all the teeth are separately picked up, it is difficult to specify which tooth has been imaged. When images are picked up by holding a video scope in one direction, it is difficult to identify the pickup data because the image is turned upside down between the back side and the surface side of the tooth, or between an upper tooth and a lower tooth in the area of the chin.

Also, since the distance between a tooth to be picked up and the video scope is prone to fluctuate, it is necessary to correct for fluctuations due to a shaking hand. Such adjustments complicate the procedure.

Also, when a tooth is cracked, it is difficult to find out the position of the crack using a pickup from one direction, and then to observe the crack.

SUMMARY OF THE INVENTION

The present invention has been achieved in the light of such points, and is directed, for example, to provide a simple, easy-to-use video scope capable of picking up an object from at least two directions at the same time, picking up an image in a short time, easily identifying the picked up data, and easily picking up a crack.

One aspect of the present invention is a video scope, comprising:
   a grip portion to be held by an operator;
   an entering portion for entering an object; and
   a pickup holding portion provided at a tip end of said entering portion, wherein said pickup holding portion is provided with picking up means of picking up an object to be picked up from at least two directions.

A video scope according to the present invention is capable of picking up an image of the object to be picked up from plural directions easily in a short time. Also, since images from plural directions are picked up at the same time, it is easy to specify which object has been picked up, and it is easy to identify data obtained by picking up.

Another aspect of the present invention is the video scope
   wherein said pickup holding portion is substantially quasi-horse-shoe or U-shaped having a central portion and two wing portions, which are located at both ends of said central portion so as to oppose to each other, and
   the picking up means has a pickup system including at least an objective lens and a solid state imaging device, and
   said picking up means is provided within said central portion of said pickup holding portion and within said two wing portions respectively.

By doing it this way, it is possible to easily pick up images of the object from three directions through the use of three pickup systems in a short time. Also, a central portion of a substantially quasi-horse-shoe-shaped pickup holding portion is caused to abut upon a portion to be picked up, whereby the distance between the object to be picked up and the pickup system is fixed, and image shaking due to shaking hands is eliminated. Therefore, it is not necessary to achieve focus, resulting in excellent operability.

Still another aspect of the present invention is the video scope
   wherein said pickup holding portion is substantially quasi-horse-shoe-shaped having a central portion and two wing portions, which are located at both ends of said central portion so as to oppose to each other, and
   the picking up means has a pickup system provided within said central portion of said pickup holding portion, including at least an objective lens and a solid state imaging device, and reflectors provided within said two wing portions respectively.

Then, in addition to the above described effects, any solid state imaging device becomes unnecessary for wing portions within the pickup holding portion, and therefore, the wing portions within the pickup holding portion become smaller in a widthwise direction, and as a result, the pickup holding portion can be miniaturized.

Yet another aspect of the present invention is the video scope wherein said pickup holding portion is substantially quasi-horse-shoe-shaped having a central portion and two wing portions, which are located at both ends of said central portion so as to oppose to each other, wherein the picking up means has a first pickup system provided within said central portion of said pickup holding portion, including at least an objective lens and a solid state imaging device, a light source provided within one of said wing portions, and a second pickup system provided within the other of said wing portions, including at least an objective lens and a solid state imaging device.

Also, by doing so, it is possible to pick up images of the object from two directions easily in a short time through the use of first and second pickup systems.

Also, the central portion of the substantially quasi-horseshoe-shaped pickup holding portion is caused to abut upon the portion to be picked up, whereby the distance between the object to be picked up and the pickup system is fixed, and image shaking due to shaking hands is eliminated, and therefore, it is not necessary to achieve focus, resulting in excellent operability.

Further, through the use of the second pickup system, transmitted light from a light source provided in one of the wing portions within the pickup holding portion is picked up, whereby it is possible to easily observe a crack in the object to be picked up.

Still yet another aspect of the present invention is the video scope further comprising an incident window for pickup light in an inner wall of said central portion of said pickup holding portion and in inner walls of said two wing portions respectively.

In the foregoing, with the provision of an incident window, the pickup holding portion can be made into an airtight or watertight structure, and therefore, it is possible to prevent any foreign matter from entering the interior of the pickup holding portion to affect the pickup system and to easily wash it.

Then, it is possible to change angles between a grip portion, an entering portion and the pickup holding portion in accordance with a shape of the portion to be picked up, resulting in excellent operability.

A further aspect of the present invention is the video scope wherein the tip end of said entering portion is bent, and said pickup holding portion is pivotally provided at the tip end of said entering portion.

Objects to be picked up with the present invention are not limited. If the object is the interior of an oral cavity and the object to be picked up is a tooth, an especially great effect will be obtained.

Any solid state imaging device may be used as long as it can be installed within the pickup holding portion and can pick up an object. For example, a CCD imaging device, a MOS type imaging device or the like can be used.

The reflector is not particularly limited, but for example, a prism mirror, a mirror or the like can be used.

Any light source may be used as long as it can be installed within the pickup holding portion and has sufficient illuminance for picking up the object. For example, a lamp, an LED or the like can be used. Of these, a white LED has lower power consumption than lamps, and has a long life, and therefore it is maintenance-free, and is preferable.

Any incident window may be used as long as it is made of material capable of guiding image pickup light. For example, glass, transparent resin or the like can be used. The shape may be the substantially quasi-horse-shoe-shaped, and windows divided in three surfaces of the pickup holding portion respectively may be used.

DESCRIPTION OF THE SYMBOLS

1 Entering Portion
2 Grip Portion
3 Pickup Holding Portion
4 Incident Window
5 Objective Lens
6 CCD Unit
7 White LED
8 Video Output Cable
9 Mirror
10 Substrate
11 Bent Entering Portion
12 Central Portion
13 Wing Portion
14 Tooth

DETAILED DESCRIPTION OF THE PREFERRED EMBODIMENTS (First Embodiment)

Next, with reference to FIGS. 1 to 3, the description will be made of a first embodiment of the present invention.

Figure 1:
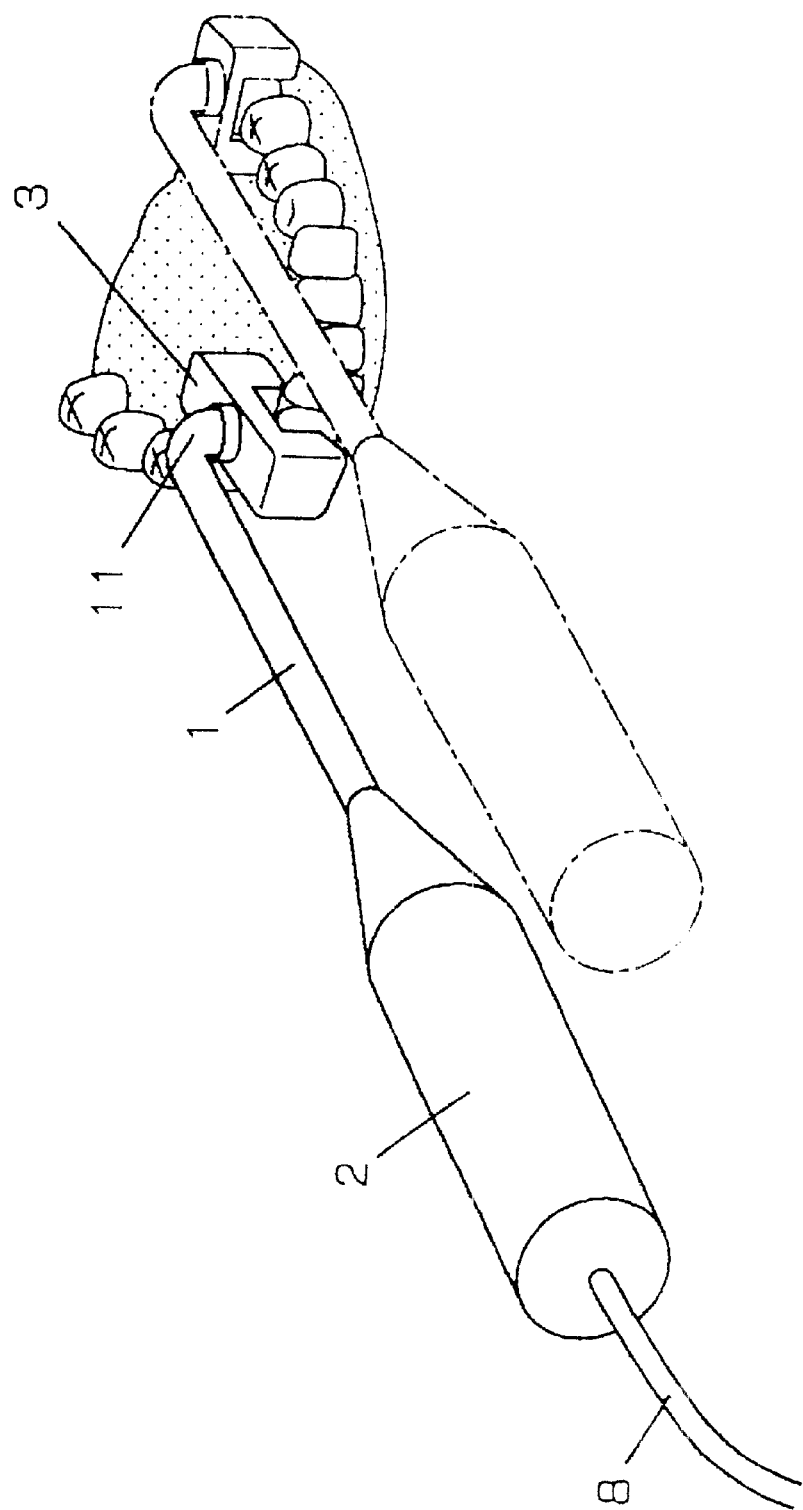
FIG. 1 is an external view showing a video scope according to an embodiment of the present invention.

FIG. 1 is an external view showing a video scope; FIG. 2 is a partially enlarged sectional view for the video scope; and FIGS. 3A to 3C are actual views showing an image of the interior of the oral cavity obtained by picking up with the same video scope.

Figure 2:
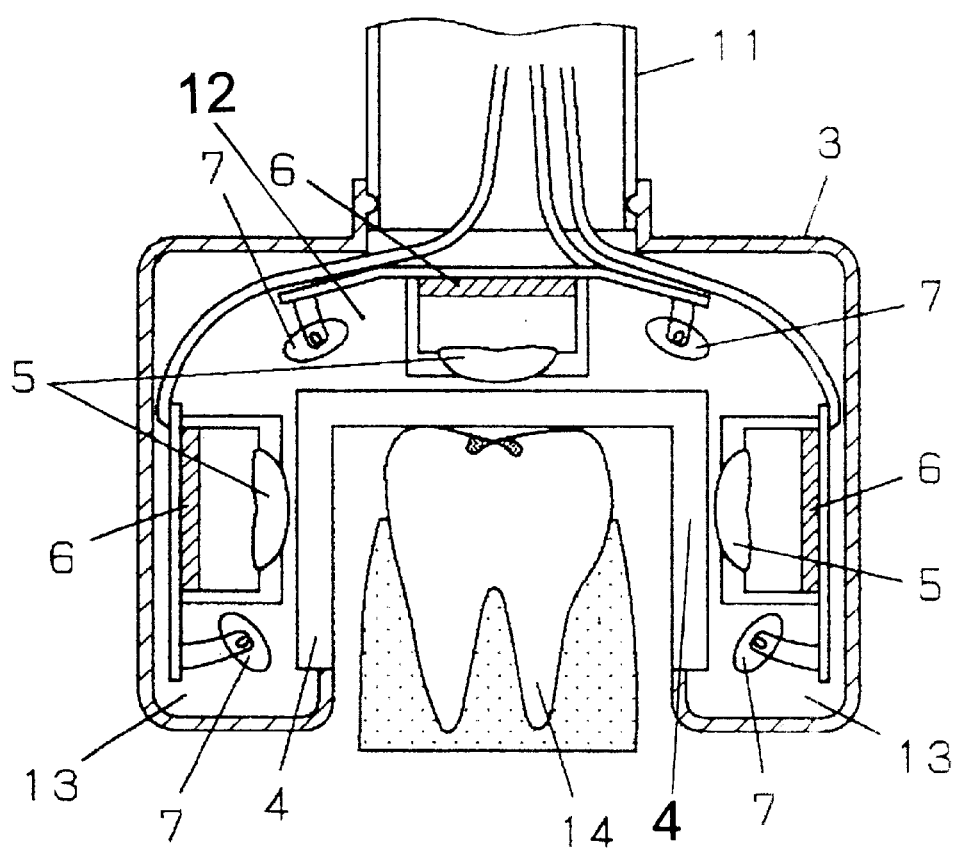
FIG. 2 is a partially enlarged sectional view for the video scope according to an embodiment of the present invention.
Figure 3A:
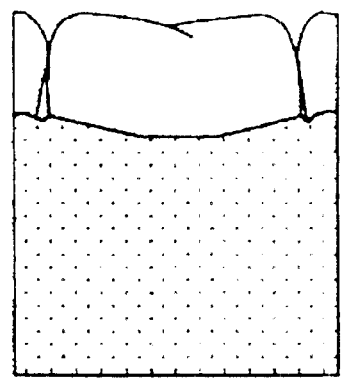
FIGS. 3A to 3C are actual views showing an image obtained by picking up with the video scope according to en embodiment of the present invention.
Figure 3B:
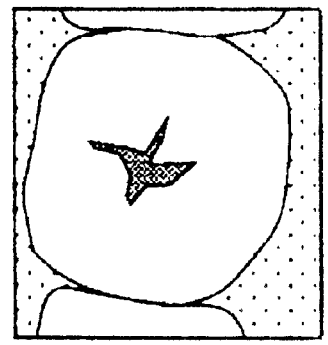
Figure 3C:
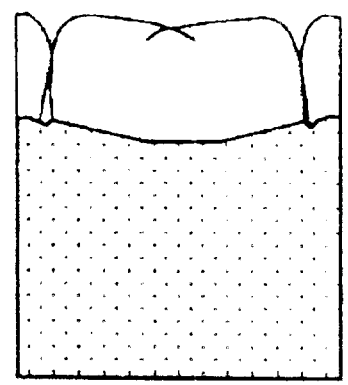

In FIGS. 1 and 2, reference numeral 1 denotes an entering portion for entering the interior of the oral cavity, which is the object; and 2, a grip portion which an operator holds in one hand. The entering portion 1 has, at its tip end portion, a bent entering portion 11 which is bent. At the tip end of the bent entering portion 11, a substantially quasi-horse-shoe or U-shaped pickup holding portion 3 is mounted air-tightly or water-tightly and pivotally with an opening side of a substantially quasi-horse-shaped directed downward. It is made into an air-tight or water-tight structure in order to prevent saliva or the like from entering. In order to enable the pickup holding portion 3 to rotate up to a position parallel to or to orthogonally intersect the entering portion 1, an angle of rotation is preferably about 180°.

On an inner wall in the central portion 12 and inner walls of two wing portions 13 in the substantially quasi-horseshoe-shaped portion of the pickup holding portion 3, there is hermetically formed an incident window 4 made of glass capable of guiding image pickup light respectively.

Further, inside the central portion 12 of the pickup holding portion 3, and inside two wing portions 13 located to oppose to each other at both ends of the central portion 12, a pickup system provided with a CCD unit 6, which is a solid state imaging device, and an objective lens 5, and a white LED 7 as a light source for throwing light are incorporated respectively, and illumination light is thrown through the incident window 4.

The objective lens 5 is provided with an iris diaphragm, but it is omitted in this figure.

In the grip portion 2, a camera circuit for operating the CCD unit 6 and the white LED 7 is incorporated, and power supply for driving the camera circuit and the white LED 7 is mounted. For this power supply, low voltage power supply such as, for example, an alkaline battery, a lithium battery and a charging type battery can be used, and a combination of a detachable battery pack and a charger may be used. The camera circuit and power supply are omitted in this figure.

From the rear of the grip portion 2, a video output cable 8 connected to a display such as a monitor TV is drawn out. This video output cable 8 is water-tightly configured over the rear from within the grip portion 2.

Also, the camera circuit and power supply need not be incorporated in the grip portion 2, but may be configured separately.

Also, as regards the angle of view, a range of about one tooth can be observed for a molar, and a range of about three teeth can be observed for a small tooth such as a fore-tooth and a canine tooth.

A video scope according to the present embodiment is capable of observing a clenched teeth surface (FIG. 3B), the back side of a tooth, which is the inner part of the oral cavity, and its gum portion (FIG. 3A), and the surface side of a tooth, which is the lip side, and its gum portion (FIG. 3C) at the same time as shown in FIG. 3 through the use of three pickup systems by inserting the entering portion 1 into the oral cavity holding the grip portion 2 to cause the pickup holding portion 3 to abut upon a tooth 14 in such a manner as to cover the tooth 14, which is the object to be picked up, with the substantially quasi-horse-shoe-shape.

Also, since images from three directions can be picked up at the same time, time required for picking up can be shortened, the consultation time can be shortened, and it is easy to specify which object has been imaged and it is easy to identify the data obtained by picking up.

At the time of observing a back tooth such as a molar, the lip is kept out of the way of the entering portion 1 by rotating the pickup holding portion 3 as shown in a chain line in FIG. 1, and therefore it is easy to use.

Also, since the pickup holding portion 3 is caused to be in contact with the tooth 14, the distance between the tooth 14 and the pickup system is fixed, no image shaking due to shaking hands is caused, there is no need for focusing, and the pickup holding portion 3 can be caused to slide along the tooth 14 while being in contact therewith. Therefore, it has excellent operability.

Also, if the system has image storing means for storing an image, the image data will be able to be simply identified.
(Second Embodiment)

Next, with reference to FIG. 4, the description will be made of a second embodiment of the present invention.

Figure 4:
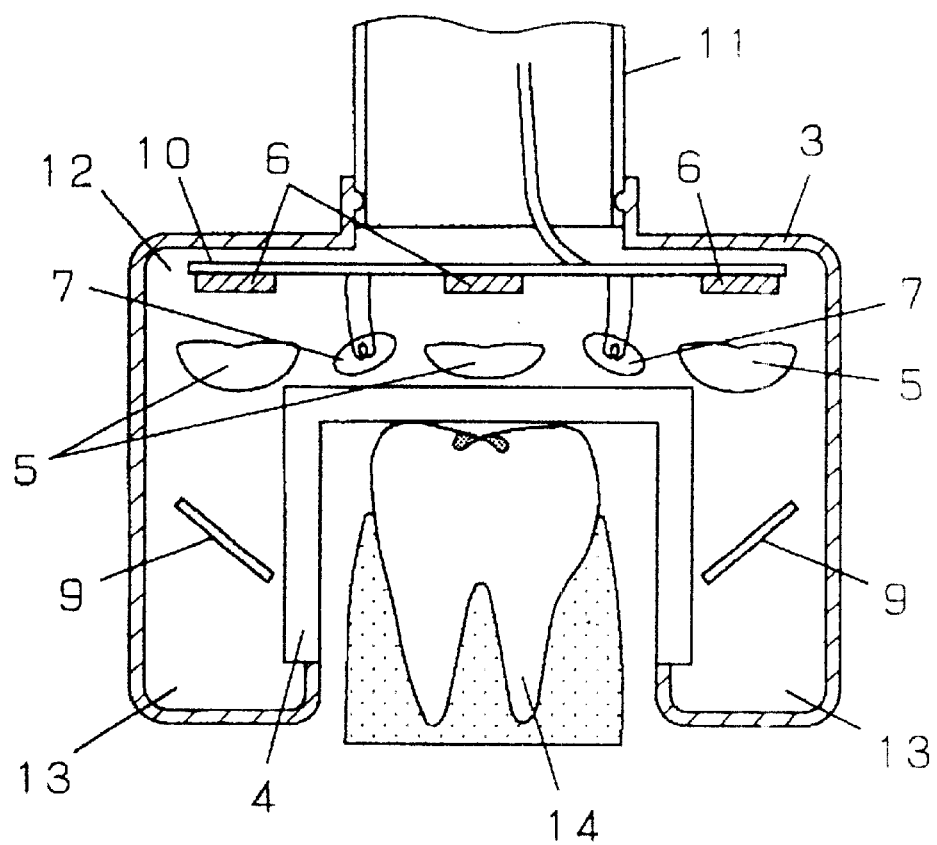
FIG. 4 is a partially enlarged sectional view for a video scope according to another embodiment of the present invention.

FIG. 4 is a partially enlarged sectional view for a video scope, and in FIG. 4, on the inner surface of a substantially quasi-horse-shoe-shaped pickup holding portion 3, an incident window 4 made of glass capable of guiding light is hermetically fixed. Reference numeral 7 denotes a white LED for throwing light, and the light is thrown through the incident window 4.

Within two wing portions 13 of the pickup holding portion 3, a mirror 9 is incorporated as a reflector for side viewing.

Also, inside the central portion 12 of the pickup holding portion 3, a pickup system provided with an objective lens 5 and a CCD unit 6, and on both sides thereof, pickup systems, each provided with an objective lens 5 for focusing an input image from a mirror 9 and a CCD unit 6 are fixed in parallel on a substrate 10 and are incorporated.

The objective lens 5 is provided with an iris diaphragm, but it is omitted in this drawing.

The configuration of portions other than the pickup holding portion 3 is the same as in the first embodiment, and as shown in FIG. 1, the pickup holding portion 3 is pivotally mounted onto a bent entering portion 11 at the tip end of the entering portion 1.

A video scope according to the present embodiment is capable of picking up images of a tooth 14 at the same time from three directions through the use of the pickup systems and two mirrors 9. The configuration of portions other than the pickup holding portion 3 is the same as in the first embodiment. Therefore, the same effects as in the first embodiment can be obtained.

In addition, three CCD units 6 are fixed onto one sheet of substrate 10, whereby the configuration of the interior of the pickup holding portion 3 and wiring are simplified. There are no CCD units within the wing portions 13 of the pickup holding portion 3. Therefore, the wing portions 13 of the pickup holding portion 3 become smaller in a widthwise direction, and as a result, the pickup holding portion can be miniaturized.

In the present embodiment, the configuration in which three CCD units 6 are fixed to the substrate 10 has been used. In place thereof, a configuration may be used in which one CCD unit is fixed onto the substrate 10, and at the central portion of the CCD unit, an image for the object to be picked up which has passed through the objective lens 5 without passing through the mirror 9 is directly inputted. At end portions of the CCD unit, an image of the object to be picked up which has passed through the objective lens 5 through the mirror 9 is inputted. At this time, the mirror 9 is set to an appropriate angle depending upon a size of the CCD unit, positions of the objective lenses or the like.
(Third Embodiment)

Next, with reference to FIGS. 5 and 6, the description will be made of a third embodiment of the present invention.

Figure 5:
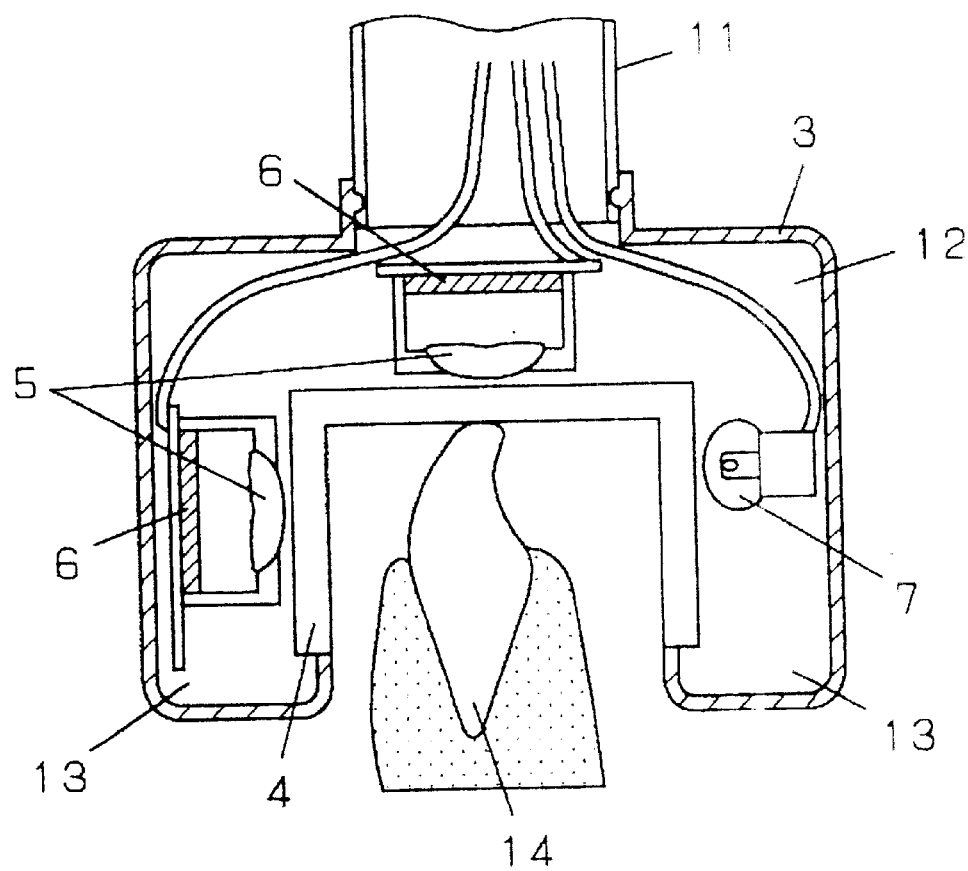
FIG. 5 is a partially enlarged sectional view for a video scope according to another embodiment of the present invention.
Figure 6:
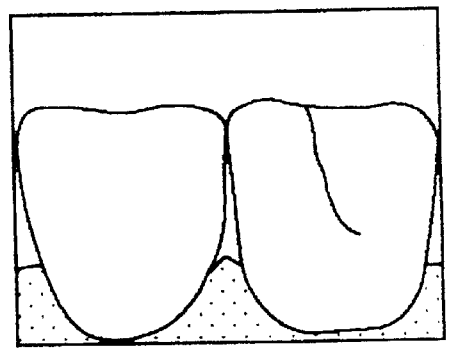
FIG. 6 is an actual view showing an image obtained by picking up with a video scope according to another embodiment of the present invention.

FIG. 5 is a partially enlarged sectional view of the video scope; and FIG. 6 is an actual view partially showing an image for the interior of the oral cavity obtained by picking up with the same video scope.

In FIG. 5, on the inner surface of the substantially quasi-horse-shoe-shaped pickup holding portion 3, an incident window 4 made of glass capable of guiding light is hermetically fixed.

Within the pickup holding portion 3, a first pickup system provided with an objective lens 5 and a CCD unit 6 is incorporated in the central portion 12, a white LED 7 as a light source is provided facing the opposite side in one of the wing portions 13, and a second pickup system provided with an objective lens 5 and a CCD unit 6 is incorporated in the other wing portion 13.

The objective lens 5 is provided with an iris diaphragm, but it is omitted in this figure.

The configuration of portions other than the pickup holding portion 3 is the same as in the first embodiment. As shown in FIG. 1, the pickup holding portion 3 is pivotally mounted onto a bent entering portion 11 at the tip end of the entering portion 1.

A video scope according to the present embodiment is capable of observing a clenched surface of teeth, the back side of a tooth, which is the inner part of the oral cavity, and its gum portion, or the surface side of a tooth, which is the lip side, and its gum portion at the same time through the use of the first and second pickup systems by inserting the entering portion 1 into the oral cavity, holding the grip portion 2 to cause the pickup holding portion 3 to abut upon a tooth 14 in such a manner as to cover the tooth 14 with the substantially quasi-horse-shoe-shaped.

Also, since images from two directions can be picked up at the same time, the time required for picking up can be shortened, the consultation time can be shortened, it is easy to specify which object has been imaged and it is easy to identify the data obtained by picking up.

Since the pickup holding portion 3 is pivotally mounted at the tip end of the entering portion 1 in the same way as the first embodiment, the lip is kept out of the way of the entering portion 1 even when a back tooth such as a molar is observed and therefore it is easy to use.

Also, since the pickup holding portion 3 is caused to be in contact with the tooth 14 in the same way as the first embodiment, the distance between the tooth 14, the pickup system is fixed. The image does not shake due to shaking hands, there is no need for focusing, and the pickup holding portion 3 can be caused to slide along the tooth 14 while being in contact therewith. Therefore, it has excellent operability.

Also, if the system has image storing means for storing an image, the image data will be able to be simply identified.

Further, through the use of the second pickup system, transmitted light from the white LED7 which has permeated the tooth 14 is picked up, whereby if the tooth 14 is cracked, its portion appears on the screen as shown in FIG. 6, and can be easily observed.

In this respect, through the use of a video scope according to the first embodiment, a white LED providing within one of the wing portions of the pickup holding portion is switched off, and through the use of the CCD unit provided there, transmitted light, which permeated the tooth, from the white LED provided within the other wing portion is picked up, whereby a crack in the tooth can be easily observed in the same way as the video scope according to the third embodiment.

As described above, a video scope according to the present invention, for example, is capable of picking up an object from at least two directions at the same time, simply and easily picking up in a short time, and easily identify the resultant data obtained by picking up.

Also, a crack on the object can be easily picked up.

What is claimed is:

1. A video scope, comprising:
   a grip portion to be held by an operator;
   an entering portion for entering an object; and
   a pickup holding portion provided at a tip end of said entering portion, wherein said pickup holding portion includes imaging means of imaging an object from at least two directions;
   wherein said pickup holding portion is substantially U-shaped having a central portion and two opposing wing portions located at respective ends of said central portion, and
   the imaging means includes a pickup system provided within said central portion including at least an objective lens and a solid state imaging device, and reflectors rovided within each of said two wing portions.

2. A video scope, comprising:
   a grip portion to be held by an operator;
   an entering portion for entering an object; and
   a pickup holding portion provided at a tip end of said entering portion, wherein said pickup holding portion includes imaging means of imaging an object from at least two directions;
   wherein said pickup holding portion is substantially U-shaped having a central portion and two opposing wing portions located at respective ends of said central portion, wherein the imaging means has a first pickup system provided within said central portion including at least an objective lens and a solid state imaging device, a light source provided within one of said wing portions, and a second pickup system provided within the other of said wing portions, including at least an objective lens and a solid state imaging device.

3. A video scope, comprising:
   a grip portion to be held by an operator;
   an entering portion for entering an object; and
   a pickup holding portion provided at a tip end of said entering portion, wherein said pickup holding portion includes imaging means of imaging an object from at least two directions;
   wherein said pickup holding portion is substantially U-shaped having a central portion and two opposing wing portions located at respective ends of said central portion, the video scope has at least three imaging means, each imaging means including at least an objective lens and a solid state imaging device, said imaging means is provided within said central portion and within each of said two wing portions, and
   further comprising an incident window for pickup of light in an inner wall of said central portion and in a respective inner wall of said two wing portions.

4. The video scope according to any one of claims 1, 2 or 3, for wherein a tip end of said entering portion is bent, and said pickup holding portion is pivotally provided at the tip end of said entering portion.

* * * * *

UNITED STATES PATENT AND TRADEMARK OFFICE
CERTIFICATE OF CORRECTION

PATENT NO.    : 6,561,972 B2
DATED         : May 13, 2003
INVENTOR(S)   : Kiyoko Ooshima et al.

It is certified that error appears in the above-identified patent and that said Letters Patent is hereby corrected as shown below:

<u>Column 8,</u>
Line 4, delete "rovided" and insert -- provided --.
Line 41, delete "for".

Signed and Sealed this

Eleventh Day of November, 2003

JAMES E. ROGAN
*Director of the United States Patent and Trademark Office*